United States Patent
Downey et al.

(10) Patent No.: US 11,617,598 B2
(45) Date of Patent: Apr. 4, 2023

(54) ULTRASONIC SURGICAL TOOL CAPABLE OF VIBRATING IN PLURAL MODES AND A DRIVE SYSTEM THAT INDUCES NON-LINEAR VIBRATIONS IN THE TOOL TIP

(71) Applicant: Stryker Corporation, Kalamazoo, MI (US)

(72) Inventors: Adam D. Downey, Kalamazoo, MI (US); Robert M. Baldwin, II, Grand Rapids, MI (US)

(73) Assignee: Stryker Corporation, Kalamazoo, MI (US)

( * ) Notice: Subject to any disclaimer, the term of this patent is extended or adjusted under 35 U.S.C. 154(b) by 792 days.

(21) Appl. No.: 16/594,671

(22) Filed: Oct. 7, 2019

(65) Prior Publication Data

US 2020/0038053 A1 Feb. 6, 2020

Related U.S. Application Data

(63) Continuation of application No. 15/425,480, filed on Feb. 6, 2017, now Pat. No. 10,561,435, which is a
(Continued)

(51) Int. Cl.
*A61B 17/32* (2006.01)
*B06B 1/02* (2006.01)
(Continued)

(52) U.S. Cl.
CPC .... *A61B 17/320068* (2013.01); *B06B 1/0276* (2013.01); *A61B 2017/0003* (2013.01);
(Continued)

(58) Field of Classification Search
CPC .... A61B 17/320068; A61B 2017/0003; A61B 2017/0011; A61B 2017/00146;
(Continued)

(56) References Cited

U.S. PATENT DOCUMENTS 5,462,522 A 10/1995 Sakurai et al.
6,066,135 A 5/2000 Honda
(Continued)

FOREIGN PATENT DOCUMENTS

CN 101254132 A 9/2008
CN 101547652 A 9/2009
(Continued)

OTHER PUBLICATIONS

English language abstract for CN 102497826 A extracted from espacenet.com database on Dec. 1, 2021, 2 pages.
(Continued)

*Primary Examiner* — Robert A Lynch
(74) *Attorney, Agent, or Firm* — Howard & Howard Attorneys PLLC

(57) ABSTRACT

An ultrasonic surgical tool system with a tip capable of simultaneously vibrating in plural modes. The system includes a console capable of supplying a drive signal to the tip that includes plural components. Each component has a frequency characteristic that is based in part on the equivalent of current through the mechanical components of the tip. The frequency components are different from each other. Based on the application of drive signal the tip undergoes non-linear vibrations.

17 Claims, 13 Drawing Sheets

Related U.S. Application Data continuation of application No. PCT/US2015/044023, filed on Aug. 6, 2015.

(60) Provisional application No. 62/034,585, filed on Aug. 7, 2014.

(51) Int. Cl.
    *B06B 1/06*     (2006.01)
    *A61B 17/00*     (2006.01)
    *A61B 17/22*     (2006.01)

(52) U.S. Cl.
    CPC .............. *A61B 2017/0011* (2013.01); *A61B 2017/0015* (2013.01); *A61B 2017/00681* (2013.01); *A61B 2017/22009* (2013.01); *A61B 2017/32007* (2017.08); *A61B 2017/320072* (2013.01); *A61B 2017/320098* (2017.08); *B06B 1/0611* (2013.01); *B06B 2201/76* (2013.01)

(58) Field of Classification Search
    CPC .. A61B 2017/0015; A61B 2017/00411; A61B 2017/00681; A61B 2017/22009; A61B 2017/32007; A61B 2017/320072; A61B 2017/320098; B06B 1/0215; B06B 1/0223; B06B 1/0276; B06B 1/0284; B06B 1/0611; B06B 1/0614; B06B 2201/76
    See application file for complete search history.

(56) References Cited

U.S. PATENT DOCUMENTS

| | | |
|---|---|---|
| 6,955,680 B2 | 10/2005 | Satou et al. |
| 7,476,233 B1 | 1/2009 | Wiener et al. |
| 9,498,245 B2 | 11/2016 | Voegele et al. |
| 9,649,147 B2 | 5/2017 | Gilbert et al. |
| 2002/0053616 A1 | 5/2002 | Rupp |
| 2004/0102709 A1 | 5/2004 | Tanaka |
| 2005/0033201 A1 | 2/2005 | Takahashi et al. |
| 2006/0281048 A1 | 12/2006 | Bailey et al. |
| 2008/0147092 A1 | 6/2008 | Rogge et al. |
| 2008/0208108 A1 | 8/2008 | Kimura |
| 2009/0325123 A1 | 12/2009 | Bailey et al. |
| 2010/0125292 A1 | 5/2010 | Wiener et al. |
| 2012/0078139 A1 | 3/2012 | Aldridge et al. |
| 2012/0209303 A1 | 8/2012 | Frankhouser et al. |
| 2012/0323265 A1 | 12/2012 | Stulen |
| 2016/0324537 A1 | 11/2016 | Green et al. |
| 2017/0071621 A1 | 3/2017 | Downey et al. |
| 2017/0143369 A1 | 5/2017 | Downey et al. |

FOREIGN PATENT DOCUMENTS

| | | |
|---|---|---|
| CN | 102497826 A | 6/2012 |
| CN | 102497827 A | 6/2012 |
| JP | H08117687 A | 5/1996 |
| JP | 2000152674 A | 5/2000 |
| JP | 2002209907 A | 7/2002 |
| WO | 2011008672 A2 | 1/2011 |
| WO | 2015021216 A1 | 2/2015 |

OTHER PUBLICATIONS

English language abstract and machine-assisted English translation for JPH 08-117687 A extracted from espacenet.com database on Jan. 27, 2021, 9 pages.

English language abstract and machine-assisted English translation for JP 2000-152674 A extracted from espacenet.com database on Jan. 27, 2021, 20 pages.

English language abstract for JP 2002-209907 A extracted from espacenet.com database on Jan. 27, 2021, 2 pages.

English language abstract for CN 101254132 extracted from espacenet.com database on Jan. 2, 2019, 2 pages.

English language abstract for CN 101547652 extracted from espacenet.com database on Jan. 2, 2019, 1 page.

English language abstract for CN 102497827 extracted from espacenet.com database on Jan. 2, 2019, 2 pages.

EPO, "PCT International Search Report and Written Opinion" for PCT/US2015/044023, dated Sep. 17, 2015.

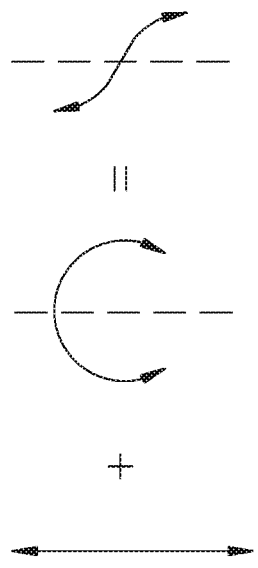
PRIOR ART
FIG. 1
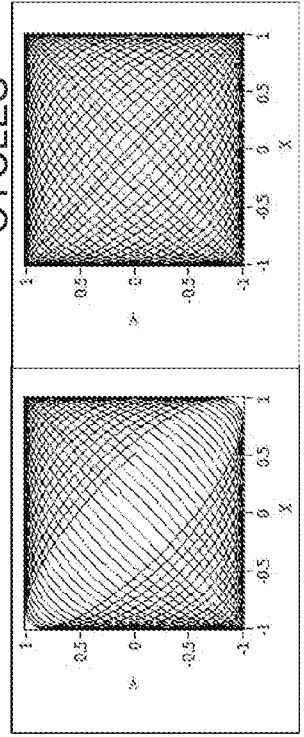
FIG. 11
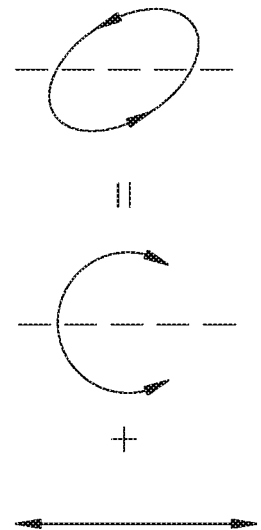

56

| | |
|---|---|
| HP ID DATA | 62 |
| STACK CAPACITAMCE | 64 |
| CURRENT $i_S^{MAX}$ | 66 |
| CURRENT $i_M^{MAX}$ | 68 |
| VOLTAGE $v_S^{MAX}$ | 70 |
| MIN DRIVE FREQ. | 72 |
| MAX DRIVE FREQ. | 74 |
| PID COEFFICIENTS | 76 |
| HP USE HISTORY | 78 |

FIG. 5

| | |
|---|---|
| TIP ID DATA | 188 |
| CURRENT $i_M^{MAX\Sigma}$ | 190 |
| POTENTIAL $V_S^{MAX1}$ | 191 |
| CURRENT $i_M^{MAX1}$ | 192 |
| POTENTIAL $V_S^{MAX2}$ | 193 |
| CURRENT $i_M^{MAX2}$ | 194 |
| MIM FREQ. COMP1 | 196 |
| MAX FREQ. COMP1 | 198 |
| TARGET FREQ COMP1 $w_{TRGT1}$ | 202 |
| VRTL IMPDNC COMP1 $M_1$ | 204 |
| MIN FREQ. COMP2 | 206 |
| MAX FREQ. COMP2 | 208 |
| TARGET FREQ COMP $w_{TRGT2}$ | 210 |
| V IMPDNC COMP1 $M_2$ | 214 |
| PID COEFFICIENTS | 216 |
| TIP USE HISTORY | 218 |

FIG. 6

ULTRASONIC SURGICAL TOOL CAPABLE OF VIBRATING IN PLURAL MODES AND A DRIVE SYSTEM THAT INDUCES NON-LINEAR VIBRATIONS IN THE TOOL TIP

RELATED APPLICATIONS

This application is a continuation of U.S. patent application Ser. No. 15/425,480 filed on Feb. 6, 2017, which is a continuation of PCT Application No. PCT/US2015/044023 filed on Aug. 6, 2015, which claims priority to U.S. Provisional Application No. 62/034,585 filed on Aug. 7, 2014, all of which are hereby incorporated herein by reference in their entirety.

FIELD OF THE INVENTION

This application is generally related to an ultrasonically driven surgical handpiece. More particularly, this invention relates to an ultrasonically driven handpiece that has plural modes of vibration and a method of driving the handpiece so the tip head undergoes non-linear vibrations.

BACKGROUND OF THE INVENTION

Ultrasonic surgical instruments are useful surgical instruments for performing certain medical and surgical procedures. Generally, an ultrasonic surgical tool includes a handpiece that contains at least one piezoelectric driver. A tip is mechanically coupled to the driver and extends forward from the housing or shell in which the driver is disposed. The tip has a head. The head is provided with features, often teeth, dimensioned to accomplish a specific medical/surgical task. An ultrasonic tool system also includes a control console. The control console supplies an AC drive signal to the driver. Upon the application of the drive signal to the driver, the driver cyclically expands and contracts. The expansion/contraction of the driver induces a like movement in the tip and more, particularly, the head of the tip. When the tip so moves, the tip is considered to be vibrating. The vibrating head of the tip is applied against tissue to perform a specific surgical or medical task. For example, some tip heads are applied against hard tissue. One form of hard tissue is bone. When this type of tip head is vibrated, the back and forth vibrations of the tip teeth, saw, remove, the adjacent hard tissue. Still other tip heads are designed to be placed against soft tissue. Some ultrasonic tools also remove tissue by inducing cavitation in the tissue and surrounding fluid. Cavitation occurs as a result of the tip head moving back and forth. Specifically, as a result of these vibrations, small voids, cavities, form in the tissue and surrounding fluid. These cavities are small zones of extremely low pressure. A pressure differential develops between the cells forming the tissue and these cavities. Owing to the relatively large magnitude of this pressure differential, the cell walls burst. The bursting of these cell walls, removes, ablates, the cells forming the tissue.

The head of an ultrasonic tip is often relatively small. Some heads have diameters of less than 1.0 cm. An ultrasonic tool essentially only removes the tissue adjacent to where the head is applied. Owing to the relatively small surface area of their heads, ultrasonic handpieces have proven to be useful tools for precisely removing both hard and soft tissue.

Most tips are designed so that when the drive signal is applied, the tip head vibrates in a single mode. Here the vibration mode is understood to be the path of travel along which the tip head travels. The majority of tips are designed to vibrate linearly. This means the heads move back and forth along an axis that is essentially in line with the proximal-to-distal longitudinal axis along the tip. Some tips are designed so that their heads, when vibrated, engage in a torsional or rotation vibration. This means that that head, when excited into vibration, rotates around the tip longitudinal axis. Still other tips are designed to flex. This means that when the tip is excited, the longitudinal axis of the tip bends back and forth. The tip head moves with the bending, the flexing, of the tip.

Problems can arise when a tip head only vibrates longitudinally. This is because this type of tip head movement frequently induces cavitation in the tissue along the tip shaft. This can be a problem when the tip is used to remove hard tissue, bone, in close proximity to soft tissue that should not be subjected to removal. Types of soft tissue that should not be removed included both blood vessels and tissue that is part of the nervous system. The problem occurs because the cavitation can result in the unwanted removal of this soft tissue.

Tips are now available that reduce this unwanted cavitation. These tips are designed to vibrate in two modes. The tip vibrates longitudinally. The tip also vibrates torsionally, around the longitudinal axis of the tip shaft. One such tip is the Long Micro Claw tip available from the Applicant, Stryker Corporation, of Kalamazoo, Mich. The structure of this tip is disclosed in U.S. Pat. No. 6,955,680, COUPLING VIBRATION ULTRASONIC HAND PIECE, the contents of which is explicitly incorporated by reference.

When a drive signal is applied to a tip capable of vibrations in different modes, the tip head undergoes a movement that is the sum of the vibratory displacements. The head of a tip capable of simultaneous longitudinal and torsional vibrations when driven, simultaneously oscillates longitudinally and rotationally. FIG. 1 depicts this movements at a point on the tip head. As a result of these simultaneous vibrations, a point on the tip head moves back and forth along a section of helix. This movement is thus proximally and distally along the longitudinal axis of the head and rotationally around the longitudinal axis.

An advantage of so vibrating the tip is that the extent the tip shaft vibrates longitudinally is reduced. This results in a like reduction in the unwanted removal of tissue adjacent the shaft.

While the above ultrasonic tool system is useful, it is not without some disadvantages. One disadvantage is that, for this system to function, the two modes of vibration have to occur at the same frequency. This requires the tip to be especially designed to vibrate in this mode. This constrains the tips to certain sizes and shapes. This can make it difficult to provide tips able to be applied to sites in order to perform certain tissue removal procedures. Further, having to design a tip to this requirement can make the tip relatively expensive to produce.

Further, when a tip head undergoes this type of movement, an individual tooth on the tip head moves back and forth on a section of helix. This movement is over a track of typically less than 300 microns in length. In practice the movement of a single tooth is along a line that is diagonal to the longitudinal axis of the tip shaft. When an individual tooth cuts into bone, the tooth forms a groove that is diagonal to this axis. The back and forth motion of the tooth in a groove places a resistance against the tip that inhibits the motion of the head other than along the directions of the groove. This resistance can be appreciable because each tooth travels in its own groove. This inhibits the ability of the practitioner to steer, position, the tip in the desired direction.

Moreover, as a result of any cutting operation, the cut material forms debris in the vicinity of the tool performing the cutting. This applies to situations when an ultrasonic surgical tool is used to remove tissue. When the teeth of an ultrasonic surgical tool move back and forth in a linear path of travel the debris tend to accumulate between the teeth. The accumulation of these debris adversely affects the ability of the teeth to dig in and remove tissue.

SUMMARY OF THE INVENTION

This invention is related to a new and useful ultrasonic surgical tool system. The system of this invention includes a tip that, when vibrated, vibrates in plural modes. The system of this invention further includes a drive system that applies a drive signal to the tip that causes the tip head to, when vibrated, move along a path of travel that is non-linear.

The system of this invention typically includes a drive system capable of providing a cumulative drive signal. This cumulative drive signal is the sum of plural distinct components. Typically the drive signal has one component for each vibration mode of the tip. In many versions of the invention, each component has a frequency characteristic. The frequency characteristic is a frequency that is at or near a target frequency of a particular vibrational mode of the tip. Here a vibration mode may be the vibration of the tip in a single plane, longitudinal, torsional or flexural. Typically, the frequency characteristics of the different vibration modes are different from each other. Alternatively, the vibration mode may be for a vibration that occurs simultaneously in two or more of planes. Here the target frequency is a frequency somewhere between and including the resonant and anti-resonant frequencies of the tip within the range of frequencies for the specific range of frequencies in which the tip is to vibrate.

It is a further feature of this invention to change the characteristics, the frequency and voltage, of each component of the drive signal. These characteristics are changed because, during use of the ultrasonic tool, the tip head is subjected to resistance, mechanical loading. This loading changes the equivalent of impedance of the mechanical component of the handpiece. The change in this characteristic of the handpiece changes how the tip head moves, vibrates, in response to the application of the drive signal. To ensure that the tip head engages in the movement desired by the practitioner, the system of this invention adjusts the drive signal. This drive signal adjustment is performed by adjusting the characteristics of the components of the drive signal.

BRIEF DESCRIPTION OF THE DRAWINGS

The invention is pointed out with particularity in the claims. The above and other features and benefits of the invention are further understood from the following Detailed Description taken in conjunction with the accompanying drawings in which:

FIG. 1 depicts the vibratory movement of a tip head when actuated using a prior art system;

FIG. 5 depicts types of data stored in the memory internal to the handpiece;

FIG. 6 depicts types of data stored in the memory integral with the tool tip;

FIG. 11 represents the movement of a single point on the head of ultrasonic tip when the tip is actuated according to this invention.

DETAILED DESCRIPTION

I. System Overview and Hardware

An ultrasonic tool system 30 that includes the features of this invention is now generally described by reference to FIGS. 2 and 3. System 30 includes a handpiece 32. A tip 142 is attached to and extends distally forward from the handpiece 32. ("Distal" is understood to mean away from the practitioner, towards the site to which the handpiece is applied. "Proximal" is understood to mean towards the practitioner holding the handpiece, away from the site to which the handpiece is applied.) Tip 142 is the component of system 30 that is applied to tissue to perform the desired medical/surgical procedure. System 30 also includes a control console 240. Control console 240 sources a drive signal that is applied to the handpiece 32. In response to application of the drive signal, handpiece 32 causes tip 142 to vibrate.

Figure 2:
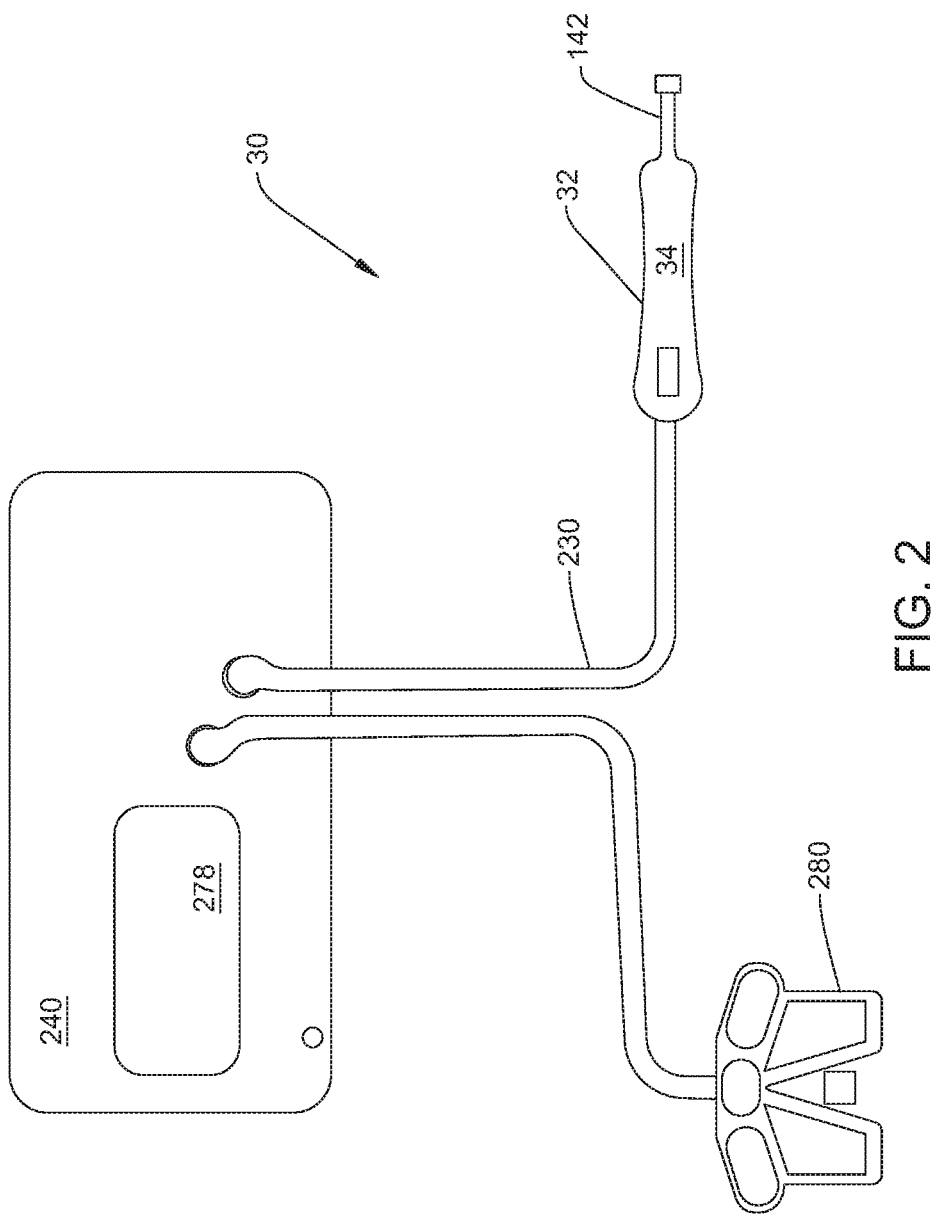
FIG. 2 depicts the basic components of an ultrasonic tool system that includes the features of this invention.

Handpiece 32 includes a body or shell 34, see only in FIG. 2. From FIGS. 3 and 4 it can be seen that one or more vibrating piezoelectric drivers 36 (four shown) are disposed inside the shell 34. Each driver 36 is formed from material that, when a current is applied to the driver, undergoes a momentary expansion or contraction. These expansions/contractions are on the longitudinal axis of a driver 36, the axis that extends between the proximally and distally directed faces of the driver. A pair of leads 38 extends away from each driver 36. Leads 38 are attached to the opposed proximally and distally directed faces of the drivers. Many, but not all, handpieces 32 include drivers 36 that are disc shaped. Drivers 36 are arranged end to end in a stack. Leads 38 are the components of system 30 over which the drive signal is applied to the drivers 36. Insulating discs 40, one shown, are disposed between adjacent drivers. In FIG. 2, drivers 36 and the insulating disc 40 are shown spaced apart from each other. This is for ease of illustrating the components. In practice drivers 36 and insulating discs 40 tightly abut.

A post 44 extends longitudinally through the drivers 36, leads 38 and insulting discs. The post 44 extends through the drivers 36, leads 38, and insulating discs 40 and along the collinear longitudinal axes of these components. Not seen are through bores internal to the drivers 36, leads 38 and insulating discs through which the post 44 extends. Post 44 projects outwardly of both the most proximally located driver 36 and the most distally located driver.

A proximal end mass 46 is located adjacent and abuts the proximally directed face of the most proximally located driver 36. Mass 46 is attached to the proximal end section of post 44. If post 44 is threaded, mass 46 may be a nut.

Figure 3:
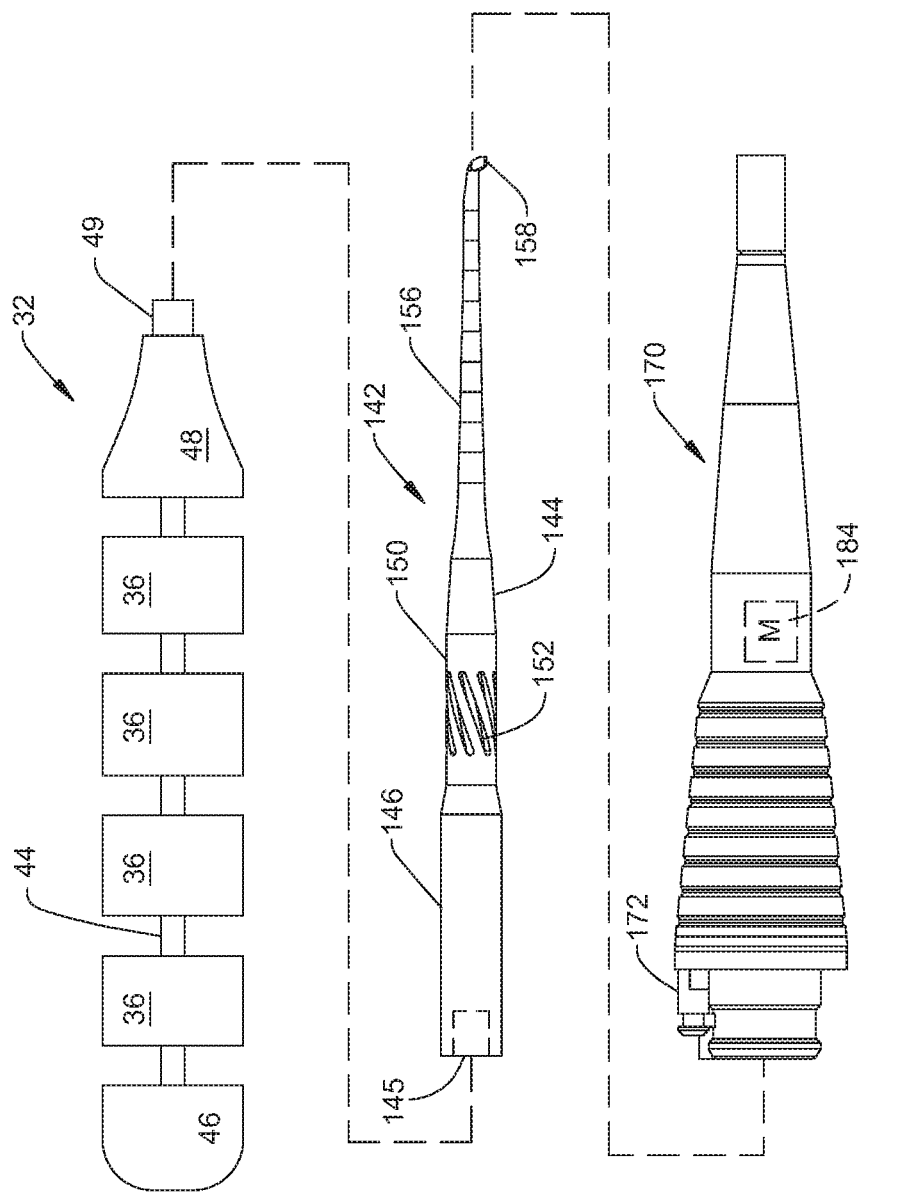
FIG. 3 is a diagrammatic and exploded depiction of the mechanical components of the tool, the handpiece, tip and sleeve of the system.

A horn 48, seen only in FIG. 3, extends forward from the distally directed face of the most distally located driver 36. Horn 48 has a base with a diameter approximately equal to the diameter of the drivers 36. Extending distally forward from the drivers 36, the diameter of the horn 48 decreases. The exposed distal end section of post 44 is affixed to the horn 48. In many versions of the invention, post 44 and horn 48 are a single piece unit. Handpiece 32 is constructed so that the stack of drivers 36 and insulating discs is compressed between proximal mass 46 and horn 48.

Also disposed in handpiece shell 34 is a handpiece memory 56. Memory 56 contains data used to regulate the operation of the handpiece 32 and tip 142. Memory 56 may take the form of an EPROM, an EEPROM or an RFID tag. The structure of the memory is not part of the invention. For purposes of illustration handpiece memory 56 is an RFID tag. A coil 54 is shown connected to memory 56. Coil 54 is the component associated with the handpiece over which the control console 240 reads from and writes to the handpiece memory 56.

FIG. 5 illustrates types of data stored in the handpiece memory 56. These data, as represented by field 62, include data identifying the handpiece 32. These data are useful for verifying that the console 240 is able to apply a drive signal to the handpiece. Data in field 62 may also indicate the type of information regarding the handpiece that is presented on the console display 278. Other data in the handpiece memory 56 are used to regulate the sourcing of drive signals to the drivers 36. While the use of these data are discussed below, the types of data are now described. Field 64 contains data indicating the capacitance $C_O$, the capacitance of the stack of drivers 36. Driver capacitance can be determined by analysis during the process of assembling the handpiece 32. Often the sum of the capacitance of the drivers is between 500 to 5000 pF. Data regarding the maximum current that should be applied to the handpiece 36, current $i_S^{MAX}$, are contained in a field 66. Current $i_S^{MAX}$ is often less than 1 Amp peak and more often 0.5 Amp peak or smaller. Field 68 contains data indicating maximum equivalent of current, $i_M^{MAX}$, that should flow through the below discussed mechanical components of the handpiece. Current $i_M^{MAX}$ is typically 0.25 Amps peak or less. The maximum potential of the drive signal, voltage $V_S^{MAX}$, are stored in field 70. Voltage $V_S^{MAX}$ is often 1500 Volts AC peak.

Also stored in handpiece memory 56 are data indicating the minimum and maximum frequencies of the drive signal that should be applied to handpiece 32. The minimum frequency, stored in field 72, is typically the minimum frequency of the drive signal that can be sourced by the control console. The maximum frequency of the drive signal, stored in field 74, is typically between 5 kHz and 40 kHz Hz greater than the minimum frequency.

Field 76 contains coefficients for filtering the control signals output by controller 96. PID control loops are used to establish the final levels for each of these signals. Field 76 contains the coefficients for each of these control loops. It should be understood that the data in fields 62, 66, 68, 70, 72, 74 and 76, like the data in field 64, are stored in the handpiece memory 56 as part of the process of assembling the handpiece.

Handpiece memory 56 also contains field 78 as a use history field. Control console 240, during use of the handpiece 32, writes data into field 128 so as to provide a log of the operation of the handpiece.

Returning to FIG. 4, it can be seen that also shown internal to the handpiece 32 are two conductors 132. Conductors 132 extend from coil 54 to the distal end of the handpiece. The conductors 132 are connected to a second coil, coil 134, also disposed in the handpiece 32.

Tip 142 extends forward from the handpiece horn 48. The tip 142 has a generally cylindrical shaft 144. In some, but not all versions of the invention, shaft 144 has plural sections each with a different cross sectional diameter. In the illustrated version of the invention, tip shaft 144 has a proximal section 146. Shaft proximal section 146 is formed with coupling features designed to facilitate the removable coupling of the tip to handpiece 32. In one version of the invention, the handpiece coupling feature is a boss 49 that extends forward from horn 48. The outer surface of the boss 49 is formed with threading (not illustrated). The tip coupling feature is a closed end bore 145 that extends inwardly from the proximal end of the shaft 144 partially through the shaft proximal section 146. Bore 145 is provided with threading (not illustrated) designed to engage the threaded boss integral with the handpiece horn 48.

In the depicted versions of the invention, shaft 144 has a middle section 150 that extends forward from the shaft proximal section 146. Middle section 150 has a diameter less than that of the proximal section 146. The depicted shaft 144 has a distal section 156. Shaft distal section 156 has a diameter less than that of the middle section 150.

A head 158 is the most distal portion of tip 142. Head 158 is located immediately forward of the shaft distal section 156. Head 158 is sometimes formed with teeth or flutes (not illustrated). Tip head 158 is the portion of system 30 pressed against tissue to perform a desired procedure. The teeth or flutes are designed so that when the head 158 moves, the teeth or flute bear against tissue. As a consequence of the movement of the head, the teeth or flutes remove tissue. The geometry of the tip teeth or flutes is not part of the present invention.

Handpiece 32 is generally designed so that the back and forth movement of the drivers induce a like vibrating motion in the tip 142. These are longitudinal vibrations in that the motion is back and forth along the longitudinal axis of the tip and, more particularly, the shaft. A tip of this invention is further provided with features that convert the proximal to distal vibratory motion applied to the proximal end of the shaft into at least two different types of vibratory motion. In the depicted tip 142 these features are helical grooves 152 that extend inwardly from the outer surface of shaft middle section 150. Owing to the presence of grooves 152, a fraction of the longitudinal motion applied to the shaft proximal section into motion that causes the sections of the tip forward of the grooves to, in addition to vibrating longitudinally, vibrate rotationally. Rotational vibration is understood to mean the vibration of the shaft and tip in an arc that extends around the longitudinal axis of the shaft 144.

The tip 142 integrated into the system 30 of this invention is further designed so that the resonant frequencies of the vibrational modes are different. Often these resonant frequencies are spaced between 200 and 2000 Hz from each other.

A sleeve 170 is disposed around tip shaft 144. Sleeve 170 is formed of plastic. The proximal end the sleeve is formed with features that facilitate the releasable coupling of the sleeve to the distal end of the handpiece horn 48. The components forming system 30 are formed so that sleeve is spaced radially away from tip shaft 144 and longitudinally away from tip head 160. More specifically the components are dimensioned so that during the normal vibration of the tip, the tip does not abut the sleeve.

While not part of the present invention, it can be seen that sleeve 170 is often formed with a fitting 172. Fitting 172 is formed to receive an irrigation line. During use of system 30, irrigating fluid is often flowed into the sleeve 170. The fluid flows around through the gap between the tip 142 and the sleeve 170 and out the open distal end of the sleeve. Handpiece post 44 and the tip 142 are formed with contiguous bores (bores not illustrated). During a procedure, suction is drawn through these bores. The suction draws from the site to which tip head 158 is applied the irrigating fluid as well as debris formed by the procedure that are entrained in the fluid. The suction also draws tissue towards the tip head 158. This drawing of the tissue towards the tip head 158 enhances the cutting of the tissue by the tip head.

Disposed inside the sleeve is a tip memory 184, seen as a dashed rectangle in FIG. 3. Memory 184 is referred to as the tip memory because, even though the memory is disposed in sleeve 170 the memory is used to control the operation of the tip 142. Further, tip 142 and sleeve 170 are typically distributed together as a single package. Tip 142 is typically initially first coupled to the handpiece 32. After the tip 142 is in place, the sleeve 170 is fitted to the handpiece. Tip memory 184 is typically the same type of memory has handpiece memory 56. Accordingly, in the illustrated version of the invention, tip memory 184 is an RFID tag. A coil 182, seen only in FIG. 4, embedded in sleeve 170 is connected to the input pins of the tip memory 184. The components forming system 30 are constructed so that when the sleeve 170 is fitted to the handpiece 32, handpiece coil 134 and coil 182 are able to engage in inductive signal exchange.

FIG. 6 depicts the type of data contained in tip memory 184. As represented by field 188, these data include a tip identification field. The data in field 188 identifies the tip and is analogous to the data identifying the handpiece in handpiece memory handpiece identification field 112. In field 190 data are stored indicating the maximum equivalent of current, $i_M^{MAXe}$, that should go through the mechanical components of the handpiece. This concept is explained below. Field 191 stores data indicating a maximum potential $V_S^{MAX1}$ for the first component of the drive signal. In a field 192 data are stored indicating the maximum equivalent of current, $i_M^{MAX1}$ that should go through the mechanical components at a first one of components of the drive signal. Field 193 stores data indicating a maximum potential $V_S^{MAX2}$ for the second component of the drive signal. Field 194 stores data indicating the maximum equivalent of current, $i_M^{MAX2}$, that should go through the mechanical components at a second one of the components of the drive signal. Field 196 contains data defining the minimum frequency of the first component of the drive signal. Field 198 contains data defining the maximum frequency of the first component of the drive signal. Field 202 contains data defining a first target frequency, $\omega_{TRGT1}$, for the first component of the drive signal. Field 204 contains a virtual impedance coefficient, $m_1$, used in associated with the target frequency for the first component of the drive signal.

Field 206 contains data defining the minimum frequency of the second component of the drive signal. Field 208 contains data defining the maximum frequency of the second component of the drive signal. Field 210 contains data defining a target frequency, $\omega_{TRGT2}$, for the second component of the drive signal. Field 214 contains a virtual impedance coefficient, $m_2$, used in associated with the target frequency for the second component of the drive signal.

A PID coefficient field 216 contains filtering coefficients for the control signals that for the tip may be more specific than the data in handpiece memory PID coefficient field 76. Tip memory 184 also contains a tip use history field 218. During operation of system 30, the control console 240 writes data to field 218 regarding use of the tip 142

Figure 4:
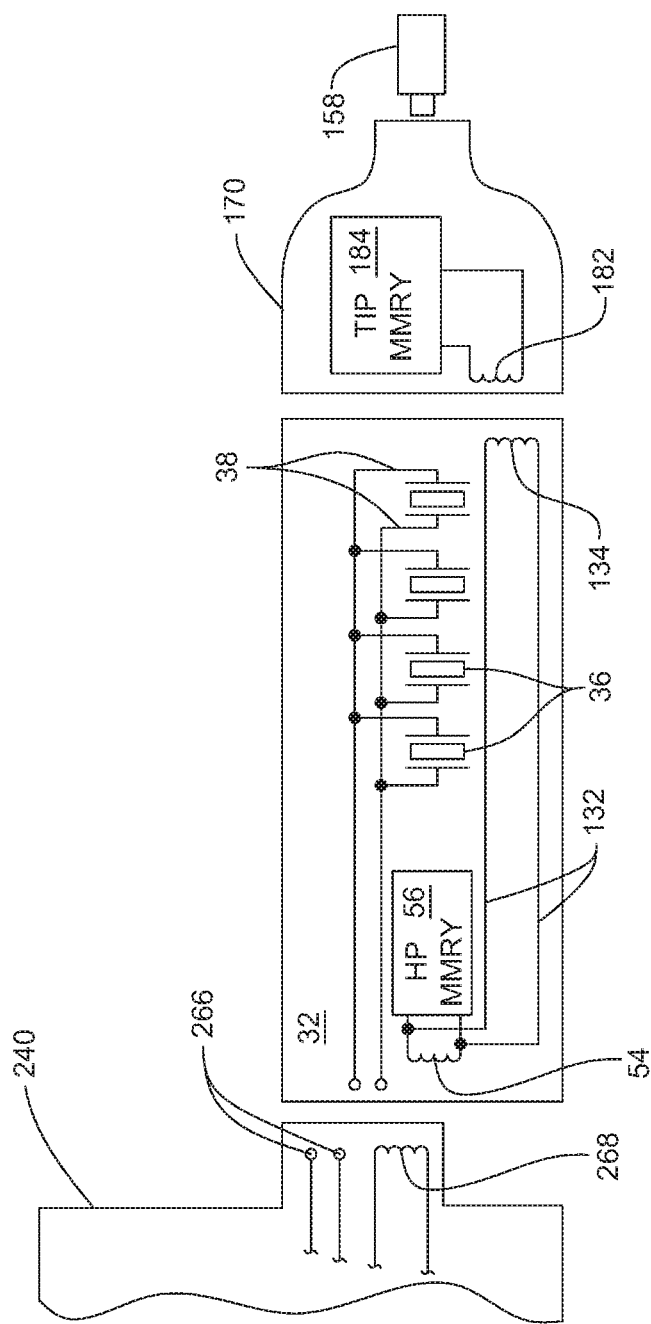
FIG. 4 is a block diagram depicting the electrical components of the handpiece and tip and how these components are connected to the control console.
Figure 7:
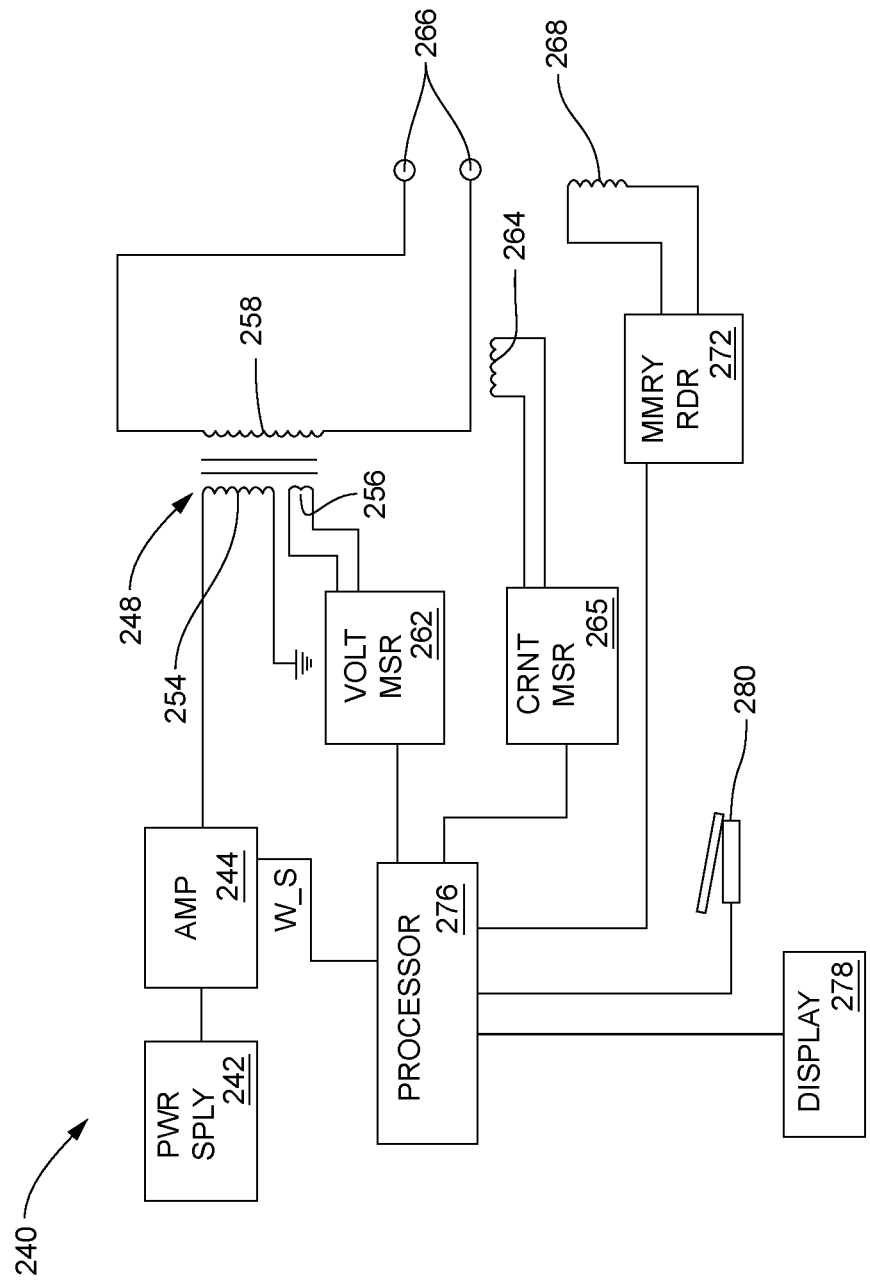
FIG. 7 is a block diagram of the electrical components of the control console and handpiece components of the system of this invention.

Control console 240, now described with respect to FIGS. 2, 4 and 7, supplies the drive signal to handpiece 32 that results in the vibration of tip 142. These components include a power supply 242. Power supply 242 outputs a constant voltage signal typically between 1 and 250 VDC. In many versions of the invention, the maximum potential of the voltage output by power supply 242 is 150 VDC or less. The voltage produced by power supply 242 is applied to a variable gain amplifier 244. A control signal, specifically a WAVEFORM_SET (W_S) signal, is applied to amplifier 244. The WAVEFORM_SET signal establishes the gain of the signal produced by the amplifier. In many versions of the invention, amplifier 244 is a variable gain Class A amplifier capable of, in response to the WAVEFORM_SET signal, outputting an AC signal. More particularly, amplifier 244 is capable of outputting a signal with a frequency of between 10 kHz and 100 kHz. Often the signal has a minimum frequency of 20 kHz.

The output signal from amplifier 244 is applied to the primary winding 254 of a transformer 248, also part of the control console 240. The voltage present across the secondary winding 258 of the transformer 248 is the drive signal applied to the handpiece drivers 36. This voltage is typically a maximum of 1500 volts AC peak. The drive signal is applied in parallel across the drivers 36.

Transformer 248 includes a tickler coil 256. The voltage present across tickler coil 256 is applied to a voltage measuring circuit 262. Based on the signal across tickler coil 256, circuit 262 produces a signal representative of the potential and phase of voltage $V_S$, the voltage of the drive signal applied to the handpiece 32. A coil 264, also disposed in control console 240, is located in close proximity to one of the conductors that extends from the transformer secondary winding 258. The signal across coil 264 is applied to a current measuring circuit 265. Circuit 265 produces a signal representative of the magnitude and phase of current is, the current of the drive signal through the handpiece.

The drive signal present across transformer secondary winding 258 is present at two conductive contacts 266 attached to a socket integral with the control console (socket not illustrated).

The drive signal is applied to the handpiece drivers by a cable 230 seen only in FIG. 1. In many constructions of system 30, handpiece 32 and cable 230 are a single unit. Cable 230 is connected to the control console socket in which contacts 266 are located.

In versions of the invention wherein the handpiece 32 and cable 230 are a single unit, handpiece coil 54 is disposed in the plug integral with the cable. Disposed in the console socket is a complementary coil 268. The components forming the system are configured so that when the plug integral with cable 230 is seated in the handpiece socket, coils 54 and 268 are able to inductively exchange signals.

The signals representative of the drive signal voltage $V_S$ and current $i_S$ are sourced to the handpiece drivers 36 are applied to a processor 276 also internal to the control console 240. Control console 240 also includes a memory reader 272. Memory reader 272 is connected at one end to console coil 268 and at an opposed end to processor 276.

The memory reader 272 converts the signals present across the coil 268 into data signals processor 276 is able to read. Memory reader 272 also, in response to signals output by the processor 276, output signals across coil 268 that cause the coil to output signals that result in the writing of data to the handpiece memory 56 and tip memory 184. The structure of memory reader 272 complements the handpiece memory 102. Thus, memory reader can be: an assembly capable of reading data in an EPROM or EEPROM or an assembly capable of interrogating and reading data from an RFID tag.

Processor 276 generates the WAVEFORM_SET signal that is applied to amplifier 244. The processor 276 thus sets the characteristics of the drive signal output by the control console 240 and applied to the handpiece 32. The characteristics of the drive signal set by processor 276 are the voltage and frequency of the drive signal. Processor 276 determines these characteristics as a function of the characteristics of the handpiece 32 and the characteristics of the tip 142. Processor 276 also determines the drive signal as a function of the acquired measurements of voltage $V_S$ and current is.

A display 278 is built into control console 240. The image on display 278 is shown as being generated by processor 276. Information depicted on display 278 includes: information identifying the handpiece 32 and the tip; and information describing characteristics of the operating state of the system. Display 278 is often a touch screen display. Processor 276 causes images of buttons to be presented on the display. By depressing the buttons, the practitioner is able to set what he/she desires as specific operating characteristics of the system 30.

In addition to the buttons presented on the display 278, there is typically at least one on on/off switch associated with the control console. In FIGS. 2 and 7, this on/off switch is represented by a footswitch 280. Footswitch 280 is configured to generate a signal that varies with the extent to which the switch is depressed. The signal is sourced to processor 276. Based on the state of the signal sourced by the footswitch 280, processor 276 regulates the generation of the drive signal so as to control both whether or not the tip vibrates and the magnitude of the tip head vibrations.

II. Fundamentals of Operation

System 30 of this invention is designed so that the control console 240 outputs a drive signal that results in the tip head 158 moving along a path of travel that can be considered non-linear. For the purposes of this invention, a non-linear path of travel is a path of travel such that when the tip head 158 oscillates back and forth, the movement of a single point of the head is along two different sets of points in space. When the tip head engages in outbound phase of a single cycle of movement, relative to a starting point, the tip head travels along a first set of the points. When the tip head engages in an inbound phase of the same cycle to return to the starting point, the tip head travels along a second set of points that is separate from the first set of points. Further, the set of points along which the tip head point travels during a first complete oscillatory cycle may be different from the set of points along which the tip head in the next oscillatory cycle. It should be understood that during an oscillatory cycle the set of points along which the tip head travels may not be in a single plane. The set of points may be in plural planes. Stated another way, the set of points may rotate around one or more axes.

Figure 8:
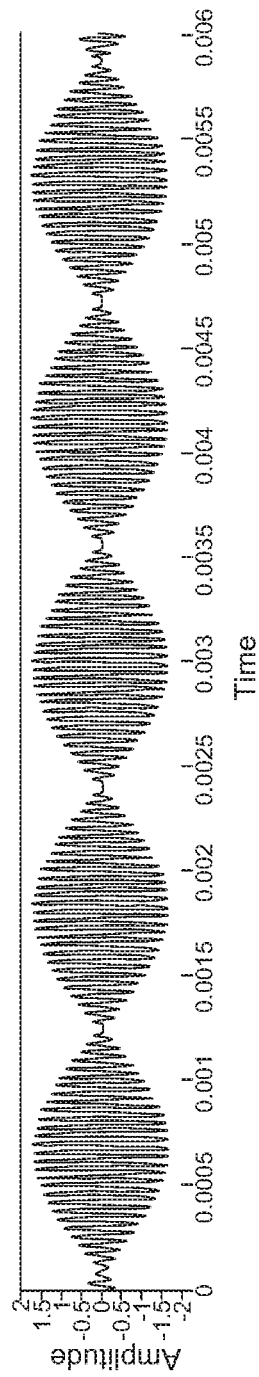
FIG. 8 depicts the waveform of the drive signal applied to the handpiece according to the system of this invention.

FIG. 8 depicts the waveform of the drive signal control console 240 outputs to the handpiece drivers 36 to induce the above-described movement of the tip head 158. The drive signal is the sum of two AC signals, referred to now as drive signal components. Each drive signal component has its own frequency and its own potential. Typically, the frequencies of these different components are different. Also, often, the potentials of the different components of the drive signal are different from each other.

It is a further feature of many versions of this invention each component of the drive signal is at a frequency that is at or near a target frequency of a particular vibrational mode of the tip. System 30 may be configured so that a vibrational mode is the vibration of the tip in a single plane, longitudinal, torsional or flexural. Here it is understood that vibration in the longitudinal plane is reciprocal movement along the longitudinal axis of the tip 142. Vibration in the torsional plane is understood to be rotational reciprocal movement of the tip head 158 in a plane perpendicular to the longitudinal axis of the tip head. Flexural movement is reciprocal movement of the tip head in a plane in which the longitudinal axis of the tip is disposed. Flexural movement is thus the bending of the tip around the shaft 144. This flexural movement can occur in any direction in the 360° around the shaft. Alternatively, the vibrational mode of the tip 42 may be a vibrational mode may be a vibration that is simultaneous reciprocal movement of the tip in two planes. For example, one vibrational mode may be longitudinal and torsional such that the motion is along a first line that is intersects the longitudinal axis of the tip shaft. The second mode may be a second combined longitudinal and torsional motion that is along a line. The difference between these two vibratory modes is that the second mode vibrations are along a line that is separate from the line of vibrations of the first mode.

The "target frequency" for a tip vibrational mode according to this invention is a frequency within the range of frequencies the tip 142 is supposed to vibrate. The target frequency typically is one of: the resonant frequency for the vibrational mode; the anti-resonant frequency for the vibrational mode; or a frequency between the resonant and anti-resonant frequencies. Since the resonant frequencies of the vibrational modes of the tip are different from each other, the target frequencies of the vibration modes are likewise understood to be different.

In many versions of the invention, the potential of each component of the drive signal is at a potential designed to foster the flow of a target equivalent of current through what are known as the mechanical components of the handpiece 32 and tip 142. These components include drivers 36, post 44, proximal end mass 46 horn 48 and tip 142. Sleeve 170 is typically not considered a component to which the equivalent of current flows. This is because, while the sleeve 170 vibrates, the vibration of the sleeve is due to the vibration of the other components. For simplification of further description, this will be further referred to simply as the equivalent of current through the mechanical components of the handpiece. This phrase will be used even though sleeve 170 can be considered a mechanical component of the handpiece 32.

Figure 9B:
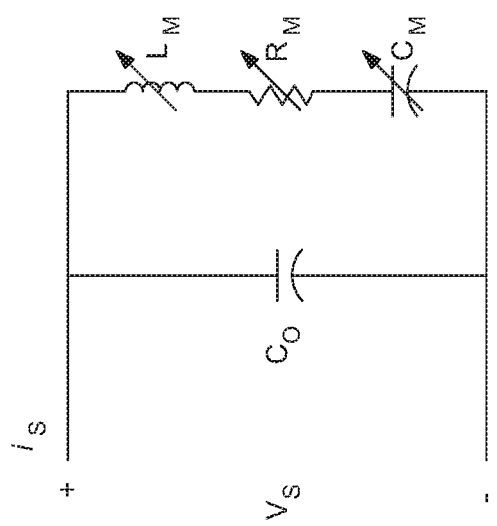
FIGS. 9A and 9B are representations of current flow through the handpiece and the impedances of the different components of the handpiece.
Figure 9A:
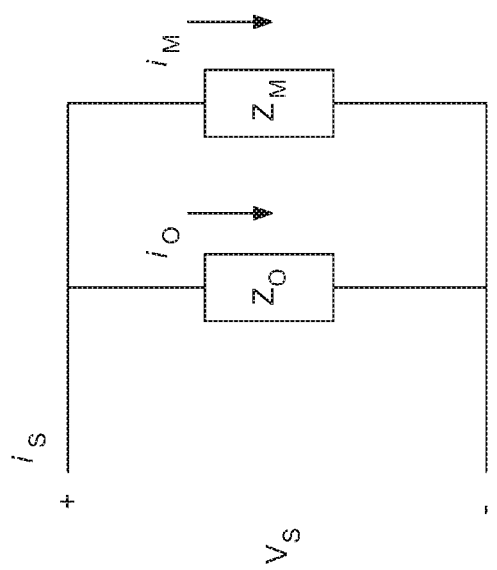

FIG. 9A is a schematic representation of how the drive signal current $i_S$ is broken down into two components. The first component is current $i_O$, the current through the handpiece drivers 36. The second component is current $i_M$, the equivalent of current through the mechanical components of the handpiece. According to Ohm's law the current through the drivers and the equivalent of current through the mechanical components of the handpiece are function of the drive signal voltage $V_S$, and the impedance of these components. In FIG. 9A, $Z_O$ is the impedance of the handpiece drivers 36. Impedance $Z_M$ is the equivalent of reactance of the mechanical components of the handpiece.

The impedance of the drivers 36 is due primarily to their capacitive reactance. Accordingly, in the schematic diagram of FIG. 9B, the driver impedance $Z_O$ is depicted as being solely a function of driver capacitance $C_O$. For the purposes of system 30 of this invention, driver capacitance $C_O$ is generally constant. The equivalence of impedance of the mechanical components of the handpiece has a resistive component, an inductive reactance component and a resistive component. Accordingly, in FIG. 9B the equivalent of mechanical impedance $Z_M$ is depicted as being a function of a resistance $R_M$, a capacitance $C_M$ and an inductance $L_M$. In FIG. 9B the mechanical equivalents of resistance $R_M$, capacitance $C_M$ and inductance $L_M$ are shown as variable. This is because these characteristics of handpiece vary as a function of the mechanical resistance to which the tip 142 is exposed when the tip is applied against tissue.

The equivalent of current that, at any one moment, flows through the mechanical components of the handpiece is determined based on the following equation:

$$i_M = i_S - j\omega C_O V_S \quad (1)$$

Here $\omega$ is the radial frequency of the drive signal. A detailed explanation of how Equation (1) is derived can be found in the Applicant's U.S. Prov. Pat. App. No. 61/863,152 filed 7 Aug. 2103, SYSTEM AND METHOD FOR DRIVING AN ULTRASONIC HANDPIECE AS A FUNCTION OF THE MECHANICAL IMPEDANCE OF THE HANDPIECE, the contents of which are published in the Applicant's also incorporated by reference PCT App. No. PCT/US2014/050034 published as WO 2015/021216 A1/US Pat. Pub. No. 2017/0071621 A1. Both of the above-listed applications are explicitly incorporated by reference into this application. As mentioned above, the drive signal supplied by system 30 of this invention has plural components. The equivalent of current through the mechanical components of the handpiece for an individual component of the drive signal is therefore based on the following equation:

$$i_{M-X} = i_{S-X} - j\omega_X C_O V_{S-X} \quad (1A)$$

The "–X" or "X" identifies the particular component of the drive signal for which the equivalent of current is being calculated.

As discussed above, system 30 of this invention is further configured to control the drive signal so that each component of the drive signal is at a frequency that, as closely as possible, tracks a target frequency of the mechanical components of the handpiece.

Generally, the relationship of the frequency of the drive signal to a target frequency can be determined by first determining the real component of the ratio of the current through the handpiece drivers 36 to the equivalent of current through the mechanical components of the handpiece. This ratio is expressed by the following Equation:

$$-\text{Re}\left\{\frac{j\omega V_S C_O}{i_S - j\omega V_S C_O}\right\} \quad (2)$$

The incorporated by reference U.S. Prov. Pat. No. 61/863,152 provides a detailed explanation of why the above ratio provides the relationship of the frequency of the drive signal to a target frequency of the mechanical components of the handpiece.

Since the drive signal applied to the handpiece drivers according to this invention is made up of plural components, the ratio for a single component is:

$$-\text{Re}\left\{\frac{j\omega_X V_{S-X} C_O}{i_{S-X} - j\omega_X V_{S-X} C_O}\right\} \quad (2A)$$

This ratio is compared to a constant target ratio (TR). The target ratio is typically a number between zero and one, inclusive. If it is the objective that the component of the drive signal be at the resonant frequency of the vibrational mode, the target ratio is zero. If it is the object that the component of the drive signal be at the anti-resonant frequency of the vibrational mode, the target ratio is one. In an implementation of this invention wherein the target frequency of the component of the drive signal be at a frequency between the resonant and anti-resonant frequencies of the vibrational mode the drive frequency is a fraction between zero and one.

There may be situations when, comparing the ratio of Equation (2A) to a target ratio, does not, by itself, provide a good indication of the relationship of the frequency of the drive signal component to the desired target frequency. This can occur as a result of the placement of the tip head 158 against tissue. More particularly, an inherent feature of some tip heads is that when they are placed against tissue and subjected to loading there are large variations in the equivalent of reactance of the mechanical components of the handpiece over the range of frequencies that includes the target frequency. Further, sometimes a practitioner may want to position the tip head 158 against tissue before actuating the handpiece 32. When this occurs, the resistive component of the equivalent of impedance of the mechanical components of the handpiece may be appreciably greater than both the capacitive reactance and the inductive reactance of this components of this impedance. In either of these situations, the below discussed step of modifying the frequency of the drive signal component so the ratio of Equation (2A) is closer to the target ratio may not result the sourcing of drive signal that has a component at a frequency close to the target frequency.

Accordingly, the below modified version of Equation (2A) is used to determine if the component of the drive signal is at a frequency that is close to the target frequency for the vibratory mode with which the component is associated:

$$-\text{Re}\left\{\frac{j\omega_X V_{S-X} C_O}{i_{S-X} - j\omega_X V_{S-X} C_O}\right\} + m_X(\omega_X - \omega_{TRGT-X})^A \approx TF \quad (2B)$$

The portion of Equation (2B) on the right side of the plus sign modifies the basic ratio as a function of the difference between the actual frequency of the component of the drive signal, $\omega_X$, and $\omega_{TRGT-X}$, the desired target frequency for the component of the drive signal. Exponent A is present because the modification may be based on a higher than first order difference between the two frequencies. Coefficient mx is the coefficient that defines the slope for defining the modification of the ratio as a function of the difference between the actual and target frequencies.

III. Actual Operation

Figure 10A:
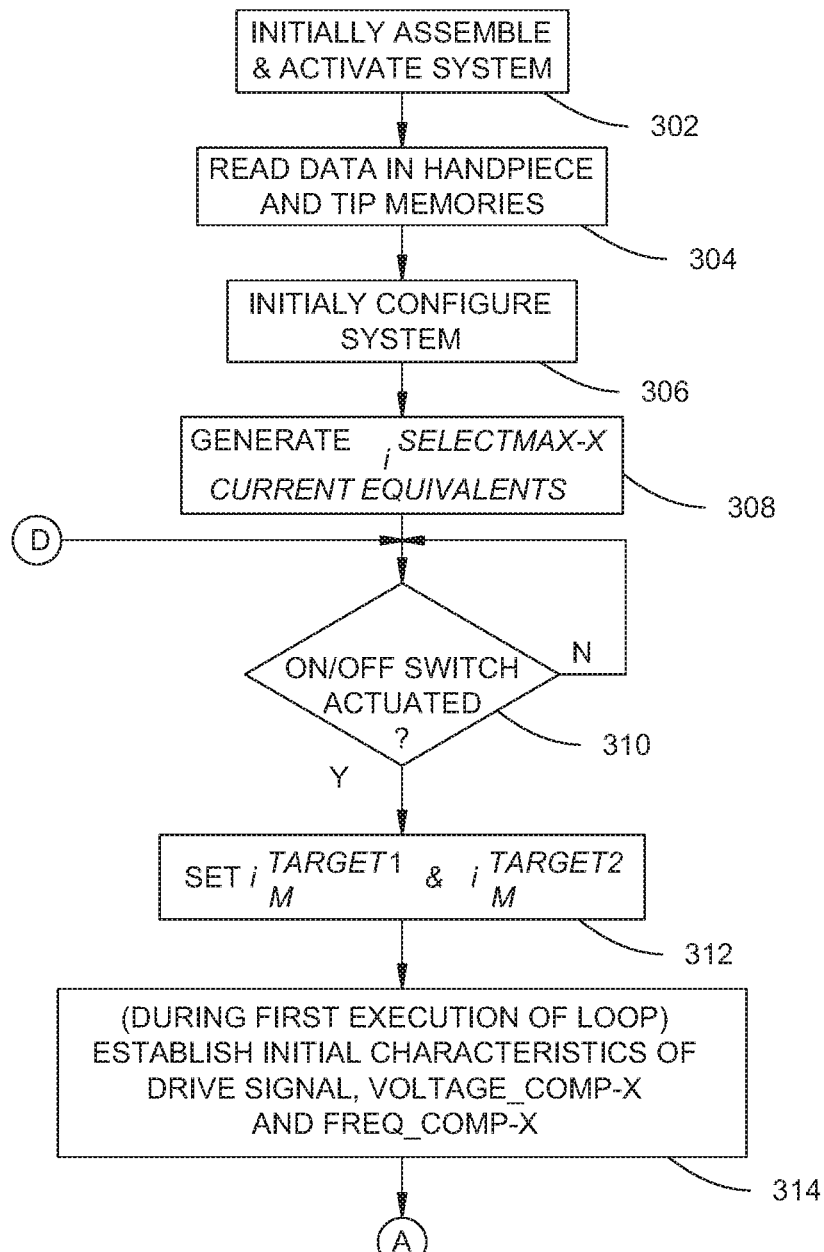
FIGS. 10A-10D, when assembled together, form a flow chart of the operation of the system of this invention.
Figure 10B:
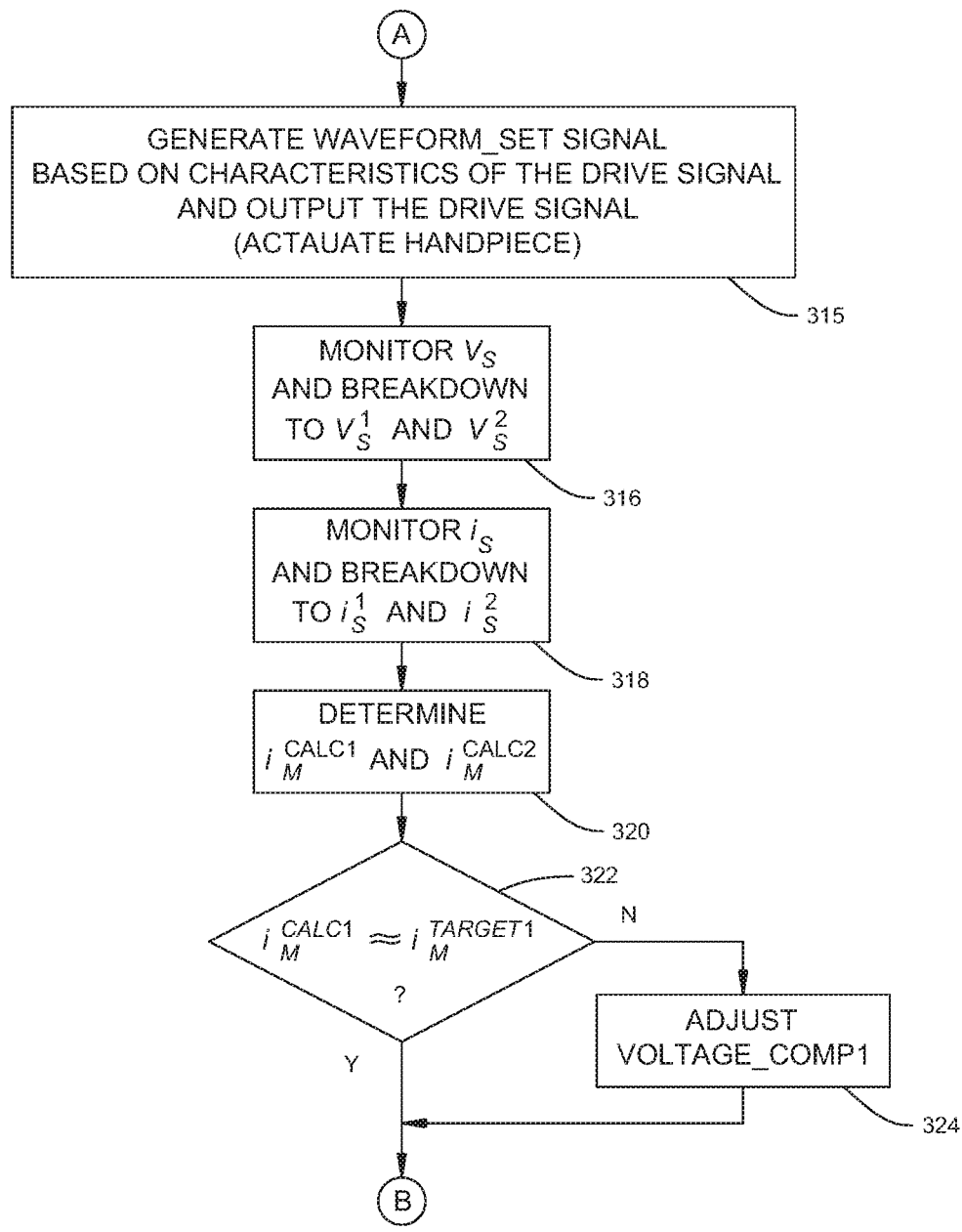
Figure 10C:
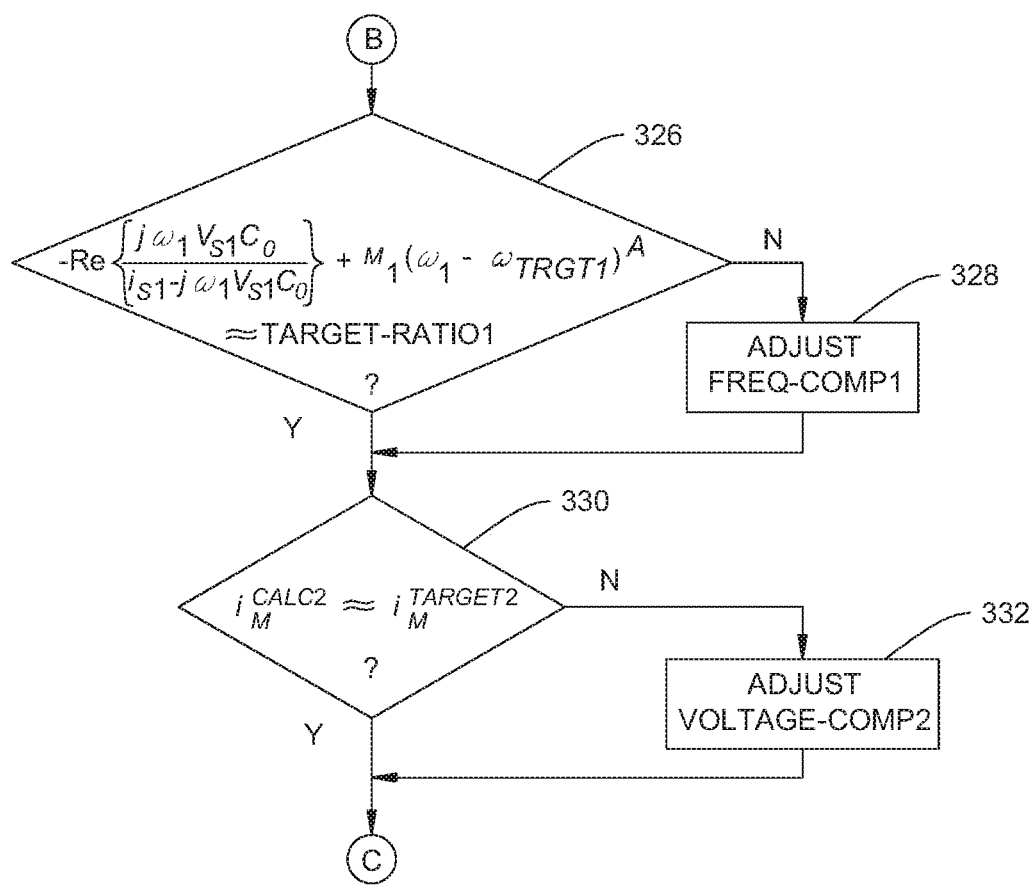
Figure 10D:
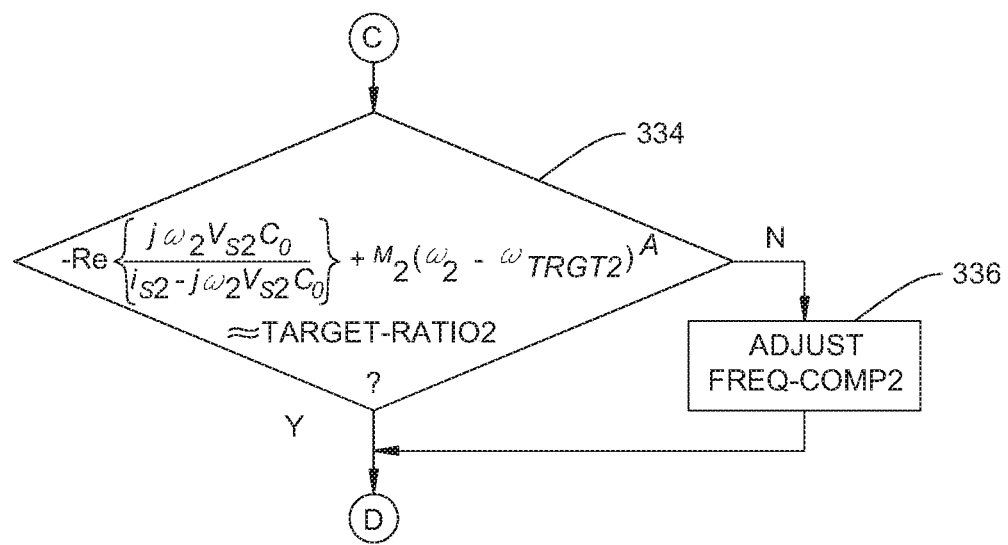

Operation of system 30 of this invention starts with the coupling of the tip 142 to the handpiece 32. Sleeve 170 is fitted over the tip and also attached to the handpiece. 32. Cable 230 is attached to the control console 240. Console 240 is then ready to be turned on. The above sub-steps form the initial assembly and activation of the system, step 302 in FIG. 10A. When the control console 240 is initially turned on, processor 276 reads the data stored in handpiece memory 56 and tip memory 184, step 304. The processor 276 receives these data by asserting the appropriate commands to the memory reader 272.

Based on the read data, in a step 306, processor completes the initial configuration of the system. Step 306 includes the performance of a number of evaluations to determine whether or not the system 30 is properly configured for use. These evaluations include: determining if the handpiece is one to which the control console 240 can supply a drive signal; and determining if tip 142 is one that is appropriate for actuation by the handpiece. These evaluations may be based on data from the handpiece identification field 62 and from the tip identification field 188. Processor 276 also evaluates whether or not the handpiece 32 and tip 142 are in conditions for use based on the read data from the handpiece use history field 78 and the tip use history field 218. An example of data indicating that use may be inappropriate are data indicating that a particular component, the handpiece or tip, has been used for a number of times or an overall time that exceeds the designed life cycle for the component.

Assuming the components are properly assembled for use as a system, processor 276 presents information to this effect on display 278. Processor 276 also invites the practitioner to enter information indicating how system should be configured to ensure that the vibratory movement of the tip head 158 is the movement desired by the practitioner. The above are all part of step 306. The receipt of the practitioner's initial configuration commands is also part of step 306.

Based on the data in the handpiece memory 56, the tip memory 184 and the practitioner entered commands, processor 276 in a step 308, establishes a selected maximum equivalent of current, $i^{SELECTMAX-X}$, through the mechanical components of the handpiece for each of the components of the drive signal. The present example of operation of the system is based on the tip 142 of FIG. 3. Specifically, this tip 142 is designed so that the drive signal induces movement of tip head 158 in two planes, longitudinal and flexural. Accordingly, the drive signal is formed from two components: a first component based on a target frequency associated with longitudinal plane vibration; and a second component based on a target frequency associated with the vibration in the torsional plane. In step 308 the selected maximum equivalent of current is established for each of the components of the drive signal using the following equation:

$$i^{SELECTMAX-X} = B_X i_M^{MAX-X} \quad (3)$$

The select maximum equivalent current is $i_X^{SELECTMAX-X}$ is understood to be based on the practitioner's setting regarding the path of travel of the tip. Coefficient $B_X$ is the coefficient processor 276 generates based on the practitioner's setting. Accordingly, a first part of the execution of step 308 is for the processor 276 to, based on the practitioner's settings, generate the appropriate $B_X$ coefficients. Coefficients $B_X$ may be generated based on reference to a look-up table. Alternatively, the $B_X$ coefficients are based on algorithms not part of this invention. These algorithms, based on the information regarding the practitioner-set path of travel, output $B_X$ coefficients that result in the generation of $i_X^{SELECTMAX-X}$ equivalent that when defining the drive signal result a drive signal being applied to the handpiece that causes the tip head to move in the desired path of travel.

In the described version of the invention, the drive signal has two components. Accordingly, in step 308 Equation (3) is executed twice. The first time the equation is executed the maximum equivalent current for the first drive signal component, the equivalent of current $i_M^{MAX1}$ from maximum current field 192 is employed as variable $i^{MAX-X}$. The second time Equation (3) is executed the equivalent of current, current $i_M^{MAX2}$, from field 194 is employed as variable $i_M^{MAX-X}$. Once the select maximum equivalents of current are generated, system 30 is ready for actuation.

Step 310 represents the processor waiting to determine if the control member has been actuated to indicate the practitioner wants to activate the handpiece, vibrate the tip head 158. In the described embodiment of the invention, processor 276 executes step 310 by monitoring the signal output by footswitch 280. When the practitioner wants to actuate the tip he/she depresses the footswitch 280. The magnitude of tip head vibrations is set by the practitioner controlling the extent to which the footswitch 280 is depressed.

Upon the processor 276 receiving signals from the footswitch indicating the switch has been depressed the processor executes step 312. In step 312 the processor 276 establishes a target equivalent of current for each of the components of the drive signal, $i_M^{TARGET1}$ and $i_M^{TARGET2}$. In many versions of the invention, each target equivalent of current is calculated using a first order equation:

$$i_M^{TARGET-X} = D i^{SELECTMAX-X} \quad (4)$$

Coefficient D is between 0.0 and 1.0, inclusive. If, for example, the practitioner wants the tip head to undergo vibrations of maximum amplitude, the footswitch 280 is typically fully depressed. Processor 276, in response to receiving signals indicating that the footswitch 280 is in this state, sets coefficient D to unity. If the practitioner wants the tip head 158 to have vibrations at less than the maximum amplitude the practitioner does not fully depress the footswitch 280. Processor 276 upon receiving a signal that the footswitch 280 is only partially depressed sets coefficient D to a value between zero and unity as a function of the extent to which the switch is depressed.

When console 240 initially executes the control loop of FIG. 10A-10D, the first execution of the loop after the evaluation of step 310 tests positive, the processor 276 executes a step 314. In step 314 the initial characteristics of the components of the drive signal are generated. The frequency of each component is referred to as variable FREQ_COMP-X. The voltage of each component is referred to as variable VOLTAGE_COMP-X. Each component of the drive signal has an initial frequency and an initial potential. The initial frequency for a component is the minimum frequency for the component as read from the tip memory 158. For the first component, this is the frequency contained in memory field 196. For the second component, this is the frequency contained in memory field 206. The initial potential is a potential that is a fraction of the maximum potential for that component of the drive signal. In some versions of the invention, the initial potential is between 0.03 and 0.07 of the maximum potential, $V_S^{MAX-X}$ for that component of the drive signal. For the first component of the drive signal the potential from tip memory field 191 is employed as $V_S^{MAX-X}$. The potential from tip memory field 193 functions as $V_S^{MAX-X}$ for the calculation of the initial potential for the second component of drive signal.

Based on the characteristics of the individual components of the drive signal, control console 240, in a step 315, then outputs the drive signal. As part of step 315, the processor 276 generates a waveform that represents the sum of the two components of the drive signal. This waveform has the appearance of the waveform of FIG. 8. The processor 276 that generates a WAVEFORM_SET signals that represent this waveform. The WAVEFORM_SET signals are then applied to the input of the amplifier 244 to which the gain control signal is supplied.

Amplifier 244, in response to receipt of the WAVEFORM_SET signal, and as part of step 315, selectively amplifies and attenuates the signal from the power supply 242. The output signal from the amplifier is applied to the transformer primary winding 254. Transformer 248 outputs the drive signal over cable 230 to the handpiece drivers 36. The above are all part of step 315.

In response to the application of the drive signals to the handpiece drivers 36, the drivers cyclically expand and contract. The expansion/contraction of the drivers is proportional to the potential of the drive signal. The expansions/contractions are proportion to the amplitude of the drive signal and at the frequency of the drive signal. Handpiece horn 48 amplifies and transfers these expansions and contractions to proximal section 146. These vibrations are along the longitudinal plane of the tip. Grooves 152 convert a fraction of this shaft movement into vibrations in the torsional plane. Owing to the varying potential of these vibrations and the structure of the tip, the tip head 158 is induced into a vibratory movement that, as depicted in FIG. 11 is non-linear. In FIG. 11, immediately to right of the leftmost equals sign, the movement as seen as the single elliptical path of travel.

In this invention, since the components of the drive signal do not have the same frequency, that paths of travel of two consecutive vibratory cycles will not be identical. This results in the tip head undergoing vibrations that in addition to not being linear, change orientations over time. The single elliptical loop of FIG. 11 should actually not be a closed loop. In FIG. 11, the middle plot to the right of the middle-located equals sign shows the path of travel of a point on the tip head after the tip head is engaged in plural vibratory cycles. In FIG. 11 the plot furthest to the right of the equals sign shows the path of the travel of the tip head point after the tip head is engaged is still more vibratory cycles. These plots indicate that, over a period of time the point on the tip head, the point on the tooth will subtend a surface. While the surface in FIG. 11 natural appears curved, it should be understood that the surface may curve around one or more axes. Implicit in this movement of the tip head point is that, in consecutive vibratory cycles, the orientation of a path of travel of the point changes.

System 30 engages in a feedback control process to ensure that the output drive signal continues to induce the desired movement of the tip head 158. To perform this control, processor 276 in step 316 monitors the voltage $V_S$ of the drive signal through the handpiece. This is the monitoring by the processor 276 of the output signal produced by voltage measuring circuit 262. As part of this monitoring, processor breaks down the voltage $V_S$ into plural components. Specifically, the voltage $V_S$ is broken down into one component for each component that comprises the drive signal. In the described version of the invention the drive signal has two components. Therefore voltage $V_S$ is broken down into a first component potential $V_S^1$ and a second component potential $V_S^2$. In some versions of the invention, processor 276 employs a Fast Fourier Transformation to so break down the components of voltage $V_S$.

As part of the feedback control, in step 318, the processor 276 monitors the drive signal current through the handpiece, current $i_S$. This monitoring is performed with the current measuring circuit 265. As with drive signal potential, drive signal current is made of plural components, one component for each component of the drive signal. Accordingly, as part of step 318, the processor breaks down the drive signal current into a first component characteristic current $i_S^1$ and a second component characteristic current $i_S^2$. In step 318, processor 276 performs a Fast Fourier Transformation to perform this break down of the measured handpiece current $i_S$ into $i_S^1$ and $i_S^2$.

In a step 320, processor determines the equivalent of current for each component of the drive signal. As this equivalent of current is calculated, not measured, it is sometimes referred to as the calculated equivalent of current. In step 320 Equation (1A) is employed to determine $i_M^{CALC1}$, the calculated equivalent of current for the first component of the drive signal and $i_M^{CALC2}$, the calculated equivalent of current for the second component of the drive signal.

The variables used to determine the calculated currents $i_M^{CALC1}$ and $i_M^{CALC2}$ include the respective potentials $V_S^1$ and $V_S^2$ for the individual components of the drive signal potentials. The above calculated first and second components current characteristics, $i_S^1$ and $i_S^2$ are also input variables into the determination of calculated equivalents of current that occurs in step 320. A third variable in each determination of calculated equivalent of current is the frequency characteristic of the component of the drive signal. For the first component of the drive signal this is $\omega_1$, for the second component this is $\omega_2$. In step 320 the frequency the frequency characteristics of the previously generated first and second components of the drive signal are employed as these variables. This means that in at least the preferred version of the invention, measured or calculated representations of the frequency characteristics are not employed as feedback data to regulate the outputting of the drive signal.

Equation (1A) has an additional variable, capacitance $C_O$ of the handpiece drivers 36. Processor 276 employs the driver capacitance read from handpiece memory field 64 as this capacitance.

In a step 322 the calculated equivalent of current for the first component of the drive signal is compared to the target equivalent of current for this component of the drive signal. This comparison is performed because if the equivalent of current is below the target equivalent of current, there is a significantly likelihood that the vibrations in the associated vibratory mode are not of sufficient amplitude to foster the desired movement of the tip head 158. If the equivalent of current to which the mechanical components of the handpiece are exposed is greater than target equivalent of current, the tip head 158 may be undergoing vibrations of an amplitude greater than that desired by the practitioner.

In some versions of the invention, the equivalent of current applied to the mechanical portions of the handpiece is fostering the desired vibrational movement if the calculated equivalent of current is within 10% or less of the target current. Alternatively, the current is of sufficient magnitude if the two currents are within 5% or less of each and ideally, within 1% or less of each other.

If the two equivalents of current are substantially equal, system 30 is in the state in which the equivalent of current flow through the mechanical components of the handpiece is at level at which the application of the drive signal assuming at the correct frequency, inducing vibrations of appropriate amplitude in tip head 52 in the associated vibratory mode. If system 30 is in this state, processor 276 proceeds to step 326.

In many situations, the comparison of step 322 indicates that calculated mechanics equivalent of current $i_M^{CALC1}$ is not substantially equal to target current $i_M^{TARGET1}$. When system 30 is in this state, processor 276 in a step 324 resets the potential characteristic of the first component of the drive signal. More specifically, the processor 276 calculates a value for potential VOLTAGE-COMP1, that would, based on Equation (3), result in an adjusted current flow through the mechanical components of the handpiece that substantially equal to target equivalent of current $i_M^{TARGET1}$. This calculation of step 324 is executed based on driver capacitance and frequency characteristic of the drive signal remaining constant.

In step 326 processor 276 determines if the frequency characteristic of the first component of the drive signal is at or substantially equal to the target frequency for this component of the drive signal. This determination is made to ensure that the frequency characteristic of the first component is resulting in the outputting of drive signal that fosters the desired movement of the tip head. In step 326 this determination is made by comparing the ratio of Equation (2B) to the target ratio. The variables used in step 318 to produce the calculated equivalent of current are used to produce this ratio. The remaining variable used to produce this ratio is the target for the frequency component. This is the $\omega_{TARGET1}$ variable from filed 202 of the tip memory 184. Coefficient $m_1$ is from coefficient field 204 of the tip memory 184. The exponent A is assumed constant and identical for all calculations generating the ratio modifier. It is within the scope of this invention that exponent A can vary.

The frequency characteristic is sometimes considered substantially equal to the target frequency characteristic if the ratio is within 10% of the target ratio. In still other versions of the invention, the frequencies are considered substantially equal of the ratio is within 5% of the target ratio and more preferably within 1% of the target ratio.

The comparison of step 326 may indicate that the frequency characteristic of first component of the drive signal is at or substantially equal to the target frequency for this component of the drive signal. This means that drive signal is inducing expansions/contractions of the drivers 36 that result in movement of the tip head at the desired pattern. If system 30 is in this state, processor 276 proceeds to execute step 330.

It may be determined in the evaluation of step 326 that the frequency characteristic of the first component of the drive signal is resulting in the output of a drive signal that does not induce the desired pattern on tip head movement. If processor 276 makes this determination, in a step 328 the processor adjusts the frequency characteristic, FREQ-COMP1, of this component of the drive signal. Owing to the ratio on the left side of Equation (2B) being negative, the calculation of step 164 yielding a negative result is, in 328 interpreted as an indication by the processor 276 that the frequency characteristic of the first component of the drive signal should be increased. If the calculation of step 326 yields a positive result, processor 276 interprets the result as indicating the handpiece is in a state in which it is necessary to decrease the frequency characteristic of the first component to increase the likelihood that the tip head is undergoing the desired path of travel.

After the execution of step 326 or, if necessary step 328, processor executes step 330. Step 330 is a comparison of the calculated equivalent of current for the second component of the drive signal to the target for this equivalent of current. Step 330 is substantially the same as step 322. The difference between steps 322 and 330 is that in step 330 calculated $i_M^{CALC2}$ is compared to target current $i_M^{TARGET2}$. Assuming the two values are substantially equal the voltage characteristic of the second component of the drive signal is not adjusted. Processor executes a step 334.

If the two values compared in step 330 are not substantially equal, in a step 332, the processor resets the voltage characteristic of the second component of the drive signal. The means by which step 332 is substantially the same as the means in employed in step 324 to reset the voltage characteristic of the first component of the drive signal. As part of step 332 processor 276 resets the WAVEFORM_SET signal based on any resetting of the voltage characteristic of the second component of the drive signal. The characteristics of the drive form likewise change.

After step 330 and if, necessary, step 332, is executed, in a step 334, the frequency characteristic of the second component of the drive signal is evaluated. This evaluation is performed using the same process used in step 326 to evaluate the frequency characteristic of the first component of the drive signal. In step 334 the variables of second component of the drive signal are applied to Equation (2B). In this use of Equation (2B), the target frequency $\omega_{TARGET2}$ from tip memory field 210 is used in the modifying component of the ratio to determine if the second component of the drive signal has an appropriate frequency characteristic. Coefficient $m_2$ from tip memory field 208 is used as the coefficient of the modifying component of the ratio. The evaluation of step 334 may indicate that the frequency characteristic of the second component of the drive signal is sufficiently equal to the target frequency. When system 30 is in this state, the processor loops back to step 310 to determine if the control member remains activated.

Alternatively, the evaluation of step 334 may indicate that frequency characteristic of the second component of the drive signal is not substantially equal to the target frequency. If system 30 is in this state, processor 276, in a step 336 resets this frequency characteristic.

Upon the execution of step 336, the processor loops back to step 310. If the evaluation of step 310 during this execution of the step indicates the on/off switch remains actuated, step 312 is reexecuted. This step is reexecuted because the practitioner may have entered commands indicating that the magnitude of the vibrations is to be reset from the previous setting.

Since the frequency and voltage characteristics of the components of the drive signal have been previously set, in this execution of the control loop, step 314 is not executed. Instead, based on the previously generated set of the drive signal component characteristics, step 315 is reexecuted. If the characteristics of the drive signal components have changed since the previous execution of step 315, this will result in processor 276 generating a new WAVEFORM_SET signal. The control console will then in turn output a new drive signal the characteristics of which have been adjusted based on the previously calculated adjustments to the characteristics of the individual components of the drive signal.

In the subsequent executions of the control loop it is understood that the reset frequency characteristics of the components of the drive signal are employed as variables $\omega_1$ and $\omega_2$ to determine if the drive signal is inducing the desired movement of the tip head 158.

Inevitably, there will be a time when the handpiece is to be deactivated. The practitioner stops actuating the on/off switch. When it is determined in step 310 that this event has occurred, the processor 276 asserts the command the result in the other components of the console 240 terminating the application of drive signal to the handpiece (steps not shown).

While not shown, it is also understood that both during the initial setting and subsequent readjustments of the WAVE-FORM_SET signal, the processor 276 ensures that the drive signal is limited by the boundary characteristics read from both the handpiece memory 56 and tip memory 184. These limits include limiting: the voltage of the drive signal based on the maximum drive signal voltage from handpiece memory field 70; the voltage characteristic of the first component of the drive signal based on the voltage data in tip memory field 191; the voltage characteristic of the second component of the drive signal based on the voltage data in tip memory field 193; the maximum current of the drive signal based on the data from the handpiece memory field 66; the maximum equivalent of current to the handpiece based on the data from handpiece memory field 68; the maximum equivalent of current for the first component of the drive signal based on the data from tip memory field 192; and the maximum equivalent of current for the second component of the drive signal based on the data from tip memory field 194.

The frequency characteristics of the drive signal is likewise set based on data read from the handpiece and tip memories 56 and 184, respectively. Thus, the data from handpiece memory fields 72 and 74 are used to define the overall boundaries of the drive signal. The frequency range data from tip memory fields 196 and 198 define the range of frequencies of the frequency characteristic of the first component of the drive signal. The frequency range data from tip memory fields 206 and 208 define the range of frequencies of the frequency characteristic of the first component of the drive signal.

As mentioned above, system 30 of this invention is configured to vibrate the tip head 158 so that, in a single vibratory cycle, a point on the tip head does not simply reciprocate back and forth along a line. Instead, the point of engages in a non-linear path of travel. When a tooth, the point of the tip head, moves against the bone, the tooth strikes the bone and immediately thereafter rubs against the bone. The striking of the bone fractures the bone to foster the removal of tissue. The immediately following action of the tooth rubbing against the bone clears the just removed material away from the bone. There is thus a short period of time between when system 30 of this invention removes bone and clears away the removed tissue. During the next vibratory cycle, only a relatively small amount of debris is present. The minimization of these debris results in a like reduction in the extent to which the presence of these debris adversely affects the bone cutting process.

When the system of this invention drives the tooth of a tip head in non-linear movement, during a single cycle, essentially the whole of the circumference of the tooth is forced against the tissue against which the tip head is placed. This tooth-against-tissue movement is what results in the desired scraping away, the removal of, the tissue. Since during a single cycle of movement essentially every surface of the tooth is forced against the tissue, each surface is exposed to at least some wear. Thus, this invention reduces the extent to which the tooth surfaces are subjected to appreciably uneven wear. It is believed that minimizing the uneven wear of the individual teeth results in a like reduction in the extent to which the cutting efficiency of the teeth are reduced. This reduces the likelihood that, in a procedure, the cutting efficiency of the set of teeth of a tip will degrade to a level that it becomes desirable, if not necessary, to replace the tip.

Moreover, since during a single cycle of movement, essentially each surface of the tooth is urged against tissue, there is no extended period of time in the cycle during which a single surface of the tooth is pressed against the tissue. This limits the frictional heating of a tooth surface that could otherwise occur if that surface is so continually pressed against tissue. The limiting of this heating reduces the extent to which this heat, if allowed to develop, could damage the tissue surrounding the tissue adjacent the tip head.

It should be further understood that system 30 can vibrate a tip in plural vibrational modes that are of different frequencies. Tips can be used with this system that are not limited to tips that, when vibrating in two modes, vibrate at a common frequency. There are appreciable manufacturing constraints and costs associated with have to provide a tip that, when it vibrates at plural modes, does so at a common frequency. These constraints and costs are typically not associated with providing a tip that, when it vibrates in plural modes, does so at different frequencies. System 30 of this invention therefore makes it more feasible both in terms of manufacturing and economics to provide different tips able to vibrate simultaneously in different modes.

A further feature of this invention is that the practitioner can set the path of the non-linear travel of the tip head. More specifically, in response to the practitioner set definition of this path of travel, processor 276, in step 308, sets the individual maximum equivalents of current, the $i^{SELECTMAX-X}$ current, for the individual vibrational modes. By setting one $i^{SELECTMAX-X}$ current to be relatively large and the second $i^{SELECTMAX-X}$ current to be relatively small, the resultant drive signal is one that will in a single cycle of tip head movement cause the tip to undergo a relatively large movement along the first vibratory path and a smaller movement in the second vibratory path. By setting the $i^{SELECTMAX-X}$ currents for the two vibrational modes to be substantially equal, the drive signal will induce movement that can result in the tip undergoing the simultaneous movement in the two different vibratory paths that are more equal in displacement.

There are times a practitioner may want to apply the tip head to tissue that is appreciably radially spaced from the longitudinal axis of the tip shaft. To perform a procedure on tissue so positioned it is desirable to provide the tip with a head that is asymmetrically located relative to the longitudinal axis of the tip shaft. Owing to this asymmetry the tip head naturally vibrates in plural modes. Typically, these vibratory modes are at different frequencies. System 30 of this invention, by regulating the vibrations in these plural modes makes it possible to ensure that when the tip head vibrates the movement is along a path of travel that is both predictable and results in the efficient removal of tissue.

Further since the tip head excited into vibration according to this invention moves in a non-linear pattern, each tooth tends to push the cut tissue away from the path of travel. This clearing of the tissue away from the teeth reduces the extent to which these debris reduce the efficiency of tissue cutting in the following vibratory cycles.

The above is directed to one version of the system of this invention. Other versions of the system of this invention may have features different from what has been described. For example, some tips of this system may have three or more vibratory modes. For this configuration of the system, the drive signal will have three or more components. It should be further understood that the target frequency characteristics for some of these components may be close to if not identical to each other. Likewise there may be times when the equivalent of current applied to the mechanical components of the handpiece may be for the different components of the drive signal substantially, if not exactly, identical.

The structure of the components of the system may vary from what has been described. Thus, in some versions of the system, internal to the console there are plural signal generators that operate simultaneously and independently from each other. The processor regulates the voltage and frequency of the signals produced by each of these signal generators. More specifically, the processor controls each signal generator so that signal generator outputs a specific component of the drive signal. These individual components are added together to produce the drive signal that is applied to the handpiece drivers 36.

In some versions of the invention the assembly that supplies the drive signal to the handpiece may not include an amplifier that varies the voltage applied to the console transformer. In these versions of the invention, the assembly that supplies signal upon which the drive signal is based included a variable current source.

It should thus be appreciated that in alternative versions of the invention, assemblies other than the disclosed coils 256 and 264 may be employed to provide the measure of the potential of the drive signal across the handpiece and the current through the handpiece. In some versions of the invention, one or more resistor networks may provide the signals upon which these measures of voltage and current and determined.

There is no requirement that in all versions of the invention driver capacitance be based on data read from a memory integral with the handpiece. In alternative versions of the invention, the processor by outputting drive signals at various frequencies and measuring the voltage and current of the drive signals determines the capacitance of the drivers.

In some versions of the invention based on performing frequency sweeps the processor determines the resonant and anti-resonant modes of each of the vibratory modes.

In some configurations of the invention, it should be understood that while the path of travel of a point of the tip head 158 is non-linear, for all intents and purposes, the path appears as a linear path.

In FIG. 11 the illustrated non-linear path is seen as a path that are essentially elliptical. This is understood to be exemplary and not limiting. Other single vibratory paths of this invention may have other shapes. These shapes include essentially circular and essentially crescent shaped. It is further within the scope of this invention that the non-linear path includes paths that cross over each other. The classic form of this type of path is the figure eight path.

In some versions of the invention the potential of one or more of the components of the drive signal may be fixed. In these versions of the invention the equivalent of current applied to the mechanical components of the handpiece is regulated by the adjustment of the target frequency associated with the component.

Further it should be understood that while generally the frequency characteristics of the components of the drive signal are different, this may not always be the case. There may be times when, based on the type of mechanical load applied to the tip 158, the frequency characteristics of the two or more components of the drive signal may be identical.

Accordingly, it is an object of the appended claims to cover all variations and modifications that come within the true spirit and scope of this invention.

What is claimed is:
1. An assembly for vibrating a tip of an ultrasonic handpiece, the handpiece having a driver to which an AC drive signal is applied to vibrate the tip, the tip being designed to vibrate in plural vibratory modes, the assembly including:
   an assembly for generating a variable AC drive signal that is applied to the driver of the handpiece;
   an assembly for measuring a voltage of the drive signal applied across the handpiece;
   an assembly for measuring a current through the handpiece; and
   a processor configured to:
      for each vibratory mode of the tip, adjust a first frequency characteristic for the vibratory mode to produce a second frequency characteristic for the vibratory mode based on the measured drive signal voltage and the measured current through the handpiece, wherein the second frequency characteristics for at least two of the vibratory modes are different from each other; and
      based on the second frequency characteristics for the vibratory modes, determine a structure of a waveform for the drive signal and assert a command based on the structure of the waveform to the assembly that generates the drive signal so as to cause the assembly to generate a drive signal that contains a component for each of the vibratory modes, each component being based on the second frequency characteristic determined for the vibratory mode.

2. The assembly of claim 1, wherein the processor is further configured to:
   for each vibratory mode of the tip, determine a calculated equivalent of current through mechanical components of the handpiece for the vibratory mode based on the first frequency characteristic for the vibratory mode, the measured drive signal voltage, and the measured current through the handpiece; and
   for each vibratory mode of the tip, adjust the first frequency characteristic for the vibratory mode to produce the second frequency characteristic for the vibratory mode based on the calculated equivalent of current through the mechanical components of the handpiece for the vibratory mode.

3. The assembly of claim 2, wherein the processor is further configured to:
   breakdown the measured current through the handpiece into plural components, each component of the measured current representing a measured current through the handpiece associated with a specific one of the vibratory modes of the tip; and
   for each vibratory mode of the tip, determine the calculated equivalent of current through the mechanical components of the handpiece for the vibratory mode based on the measured current through the handpiece associated with the vibratory mode.

4. The assembly of claim 3, wherein the processor is further configured to, for each vibratory mode of the tip, determine the calculated equivalent of current through the mechanical components of the handpiece for the vibratory mode by determining a difference between the measured current through the handpiece associated with the vibratory mode and a current through the driver associated with the vibratory mode.

5. The assembly of claim 4, wherein the processor is further configured to, for each vibratory mode of the tip, determine the current through the driver associated with the vibratory mode based on a capacitance of the driver, a component of the measured drive signal voltage associated with the vibratory mode, and the first frequency characteristic for the vibratory mode.

6. The assembly of claim 5, wherein the processor is further configured to read the capacitance of the driver from a memory device included with the tip.

7. The assembly of claim 3, wherein the processor is further configured to:
for each vibratory mode of the tip:
determine a ratio for the vibratory mode of current through the driver associated with the vibratory mode to the equivalent of current through the mechanical components of the handpiece for the vibratory mode; and
adjust the first frequency characteristic for the vibratory mode to produce the second frequency characteristic for the vibratory mode based on the ratio for the vibratory mode.

8. The assembly of claim 7, wherein the processor is further configured to:
for each vibratory mode of the tip:
determine if a real part of the ratio for the vibratory mode is substantially equal to a target value; and
adjust the first frequency characteristic for the vibratory mode to produce the second frequency characteristic for the vibratory mode responsive to the real part of the ratio for the vibratory mode not being substantially equal to the target value.

9. The assembly of claim 8, wherein the target value is zero.

10. The assembly of claim 7, wherein the processor is further configured to:
for each vibratory mode of the tip:
generate a modified value based on the ratio for the vibratory mode, the first frequency characteristic for the vibratory mode, and a target frequency for the vibratory mode;
determine whether the modified value is substantially equal to a target value; and
adjust the first frequency characteristic for the vibratory mode to produce the second frequency characteristic for the vibratory mode responsive to the modified value not being substantially equal to the target value.

11. The assembly of claim 10, wherein the processor is further configured to, for each vibratory mode of the tip, generate the modified value by modifying a real part of the ratio for the vibratory mode as a function of a difference between the first frequency characteristic for the vibratory mode and the target frequency for the vibratory mode.

12. The assembly of claim 2, wherein the processor is further configured to:
breakdown the measured drive signal voltage into plural components, each component of the measured drive signal voltage representing a measured voltage across the handpiece associated with a specific one of the vibratory modes of the tip; and
for each vibratory mode of the tip, determine the calculated equivalent of current through the mechanical components of the handpiece for the vibratory mode based on the measured voltage across the handpiece associated with the vibratory mode.

13. The assembly of claim 1, wherein as a result of application of the drive signal that contains a component for each of the vibratory modes to the driver, a head of the tip engages in a non-linear path of travel in a single vibratory cycle.

14. The assembly of claim 1, wherein as a result of application of the drive signal that contains a component for each of the vibratory modes to the driver, a head of the tip travels in a loop in a single vibratory cycle.

15. The assembly of claim 1, wherein the processor is further configured to establish the first frequency characteristic for each vibratory mode based on data retrieved from a memory device included with the tip.

16. An assembly for vibrating a tip of an ultrasonic handpiece, the handpiece having a driver to which an AC drive signal is applied to vibrate the tip, the tip being designed to vibrate in plural vibratory modes, the assembly including:
an assembly for generating a variable AC drive signal that is applied to the driver of the handpiece;
an assembly for measuring a voltage of the drive signal applied across the handpiece;
an assembly for measuring a current through the handpiece; and
a processor configured to assert a command to the assembly that generates the drive signal based on the measured drive signal voltage and the measured current through the handpiece so as to cause the assembly to generate a drive signal that contains a component for each of the vibratory modes, each component being based on a frequency characteristic determined for the vibratory mode such that the tip moves in a non-linear path of travel in a single vibratory cycle.

17. A method for vibrating a tip of an ultrasonic handpiece, the handpiece having a driver to which an AC drive signal is applied to vibrate the tip, the tip being designed to vibrate in plural vibratory modes, the method comprising:
generating a variable AC drive signal that is applied to the driver of the handpiece;
measuring a voltage of the drive signal applied across the handpiece;
measuring a current through the handpiece;
for each vibratory mode of the tip, adjusting a first frequency characteristic for the vibratory mode to produce a second frequency characteristic for the vibratory mode based on the measured drive signal voltage and the measured current through the handpiece, wherein the second frequency characteristics for at least two of the vibratory modes are different from each other;
based on the second frequency characteristics for the vibratory modes, determining a structure of a waveform for the drive signal; and
based on the structure of the waveform, generating a drive signal that is applied to the driver of the handpiece and contains a component for each of the vibratory modes, each component being based on the second frequency characteristic determined for the vibratory mode.

* * * * *